(12) United States Patent
Baker et al.

(10) Patent No.: US 10,981,018 B2
(45) Date of Patent: Apr. 20, 2021

(54) RADIOACTIVE SEED LOADING APPARATUS

(71) Applicant: GT Medical Technologies, Inc., Mesa, AZ (US)

(72) Inventors: John Baker, Gilbert, AZ (US); David Brachman, Phoenix, AZ (US)

(73) Assignee: GT MEDICAL TECHNOLOGIES, INC., Tempe, AZ (US)

( * ) Notice: Subject to any disclaimer, the term of this patent is extended or adjusted under 35 U.S.C. 154(b) by 72 days.

(21) Appl. No.: 16/275,941

(22) Filed: Feb. 14, 2019

(65) Prior Publication Data
US 2020/0261740 A1    Aug. 20, 2020

(51) Int. Cl.
*A61N 5/10*    (2006.01)

(52) U.S. Cl.
CPC ...... *A61N 5/1007* (2013.01); *A61N 2005/101* (2013.01); *A61N 2005/1009* (2013.01); *A61N 2005/1024* (2013.01)

(58) Field of Classification Search
None
See application file for complete search history.

(56) References Cited

U.S. PATENT DOCUMENTS

| D244,393 S | 5/1977 | Collica et al. |
|---|---|---|
| 4,706,652 A | 11/1987 | Horowitz |
| 4,754,745 A | 7/1988 | Horowitz |
| 4,946,435 A | 8/1990 | Suthanthiran et al. |
| 5,030,195 A | 7/1991 | Nardi |
| D381,080 S | 7/1997 | Ohata |
| 5,772,574 A | 6/1998 | Nanko |
| 5,803,895 A | 9/1998 | Kronholz et al. |
| 5,840,008 A | 11/1998 | Klein et al. |
| 5,871,708 A | 2/1999 | Park et al. |
| D408,957 S | 4/1999 | Sandor |
| 5,967,966 A | 10/1999 | Kronholz et al. |
| 5,997,842 A | 12/1999 | Chen |
| 6,017,482 A | 1/2000 | Anders et al. |
| D420,452 S | 2/2000 | Cardy |
| D420,745 S | 2/2000 | Cardy |
| D420,746 S | 2/2000 | Cardy |

(Continued)

FOREIGN PATENT DOCUMENTS

| BR | 11 2013 027841 2 | 4/2012 |
|---|---|---|
| CA | 2835065 | 2/2018 |

(Continued)

OTHER PUBLICATIONS

Cole, P.D., et al., "A comparative long-term assessment of four soft tissue supplements". Anesthetic Surg J. 31(6). 674-681, 2011.

(Continued)

*Primary Examiner* — Christine H Matthews
(74) *Attorney, Agent, or Firm* — Knobbe, Martens, Olson & Bear LLP (57) ABSTRACT

A loading apparatus is usable to embed radioactive seeds into carriers, while limiting exposure of the user to radioactive energy from the radioactive seeds. The loading apparatus facilitates accurate positioning of radioactive seeds within a carrier. The illustrated loaders comprise two components, a base and a lid, although in other embodiments the loaders may be separated into additional components.

15 Claims, 8 Drawing Sheets

(56) References Cited

U.S. PATENT DOCUMENTS

| | | | |
|---|---|---|---|
| 6,129,670 A | 10/2000 | Burdette et al. |
| D443,061 S | 5/2001 | Bergstrom et al. |
| 6,248,057 B1 | 6/2001 | Mavity et al. |
| 6,327,490 B1 | 12/2001 | Spetz |
| 6,358,195 B1 | 3/2002 | Green et al. |
| 6,360,116 B1 | 3/2002 | Jackson et al. |
| 6,385,477 B1 | 5/2002 | Werner et al. |
| 6,450,937 B1 | 9/2002 | Mercereau et al. |
| 6,471,631 B1 | 10/2002 | Slater et al. |
| 6,512,943 B1 | 1/2003 | Kelcz |
| 6,547,816 B1 | 4/2003 | O'Foghludha |
| 6,712,508 B2 | 3/2004 | Nilsson et al. |
| D488,864 S | 4/2004 | Fago et al. |
| 6,787,042 B2 | 9/2004 | Bond et al. |
| 7,011,619 B1 | 3/2006 | Lewis |
| 7,118,729 B1 | 10/2006 | O'Foghludha |
| D561,896 S | 2/2008 | Jones |
| D580,056 S | 11/2008 | Orthner |
| D580,057 S | 11/2008 | Ramadani |
| 7,776,310 B2 | 8/2010 | Kaplan |
| 8,039,790 B2 | 10/2011 | Cho et al. |
| D657,474 S | 4/2012 | Dona |
| D680,649 S | 4/2013 | Jagger et al. |
| D681,210 S | 4/2013 | Beiriger et al. |
| D681,812 S | 5/2013 | Farris et al. |
| D681,813 S | 5/2013 | Jagger et al. |
| D686,341 S | 7/2013 | Nakaji et al. |
| D686,744 S | 7/2013 | Nakaji et al. |
| D686,745 S | 7/2013 | Nakaji et al. |
| D686,746 S | 7/2013 | Nakaji et al. |
| D686,747 S | 7/2013 | Nakaji et al. |
| D686,748 S | 7/2013 | Nakaji et al. |
| D687,568 S | 8/2013 | Nakaji et al. |
| D687,966 S | 8/2013 | Nakaji et al. |
| D687,967 S | 8/2013 | Nakaji et al. |
| 8,600,130 B2 | 12/2013 | Eriksson Järliden |
| 8,605,966 B2 | 12/2013 | Eriksson Järliden |
| 8,825,136 B2 | 9/2014 | Giller et al. |
| 8,876,684 B1 | 11/2014 | Nakaji et al. |
| 8,939,881 B2 | 1/2015 | Nakaji et al. |
| 8,974,364 B1 | 3/2015 | Nakaji et al. |
| 9,022,915 B2 | 5/2015 | Nakaji et al. |
| 9,403,033 B1 | 8/2016 | Brachman |
| 9,409,038 B2 | 8/2016 | Nakaji et al. |
| 9,492,683 B2 | 11/2016 | Brachman et al. |
| 9,526,463 B2 | 12/2016 | Brachman et al. |
| 9,545,525 B2 | 1/2017 | Nakaji et al. |
| 9,788,909 B2 | 10/2017 | Larkin et al. |
| 9,789,608 B2 | 10/2017 | Itkowitz et al. |
| 9,821,174 B1 | 11/2017 | Fram et al. |
| 10,080,909 B2 | 9/2018 | Brachman et al. |
| 10,085,699 B2 | 10/2018 | Brachman et al. |
| 10,265,542 B2 | 4/2019 | Brachman et al. |
| 10,350,431 B2 | 7/2019 | Nakaji et al. |
| 2001/0044567 A1 | 11/2001 | Zamora et al. |
| 2002/0058854 A1 | 5/2002 | Creed et al. |
| 2002/0120174 A1* | 8/2002 | Steele, Sr. ............ A61N 5/1007 600/7 |
| 2003/0045769 A1 | 3/2003 | Kalas et al. |
| 2003/0088141 A1 | 5/2003 | Terwilliger et al. |
| 2003/0130573 A1 | 7/2003 | Yu et al. |
| 2003/0149329 A1 | 8/2003 | O'Foghludha |
| 2003/0208096 A1 | 11/2003 | Tam |
| 2004/0091421 A1 | 5/2004 | Aston et al. |
| 2004/0109823 A1 | 6/2004 | Kaplan |
| 2004/0116767 A1 | 6/2004 | Lebovic et al. |
| 2004/0242953 A1 | 12/2004 | Good |
| 2005/0035310 A1 | 2/2005 | Drobnik et al. |
| 2005/0244045 A1 | 11/2005 | Eriksson |
| 2005/0267319 A1 | 12/2005 | White et al. |
| 2006/0015030 A1 | 1/2006 | Poulin et al. |
| 2006/0063962 A1 | 3/2006 | Drobnik et al. |
| 2006/0173236 A1 | 8/2006 | White et al. |
| 2006/0235365 A1 | 10/2006 | Terwilliger |
| 2006/0253048 A1 | 11/2006 | Jones |
| 2007/0190761 A1 | 8/2007 | Dunkley et al. |
| 2007/0225544 A1 | 9/2007 | Vance et al. |
| 2008/0004714 A1 | 1/2008 | Lieberman |
| 2008/0009661 A1 | 1/2008 | Lamoureux et al. |
| 2008/0058580 A1 | 3/2008 | Black et al. |
| 2008/0146861 A1 | 6/2008 | Murphy et al. |
| 2008/0221384 A1 | 9/2008 | Chi Sing et al. |
| 2009/0012347 A1 | 1/2009 | Helle |
| 2009/0069625 A1 | 3/2009 | Helle et al. |
| 2009/0131735 A1 | 5/2009 | Drobnik et al. |
| 2009/0156880 A1 | 6/2009 | Allan et al. |
| 2009/0253950 A1 | 10/2009 | Rapach et al. |
| 2009/0271715 A1 | 10/2009 | Tumuluri |
| 2009/0275793 A1 | 11/2009 | Black et al. |
| 2010/0056908 A1 | 3/2010 | Giller et al. |
| 2010/0200778 A1 | 8/2010 | Drobnik et al. |
| 2010/0228074 A1 | 9/2010 | Drobnik et al. |
| 2010/0268015 A1 | 10/2010 | Drobnik et al. |
| 2010/0288916 A1 | 11/2010 | Cho et al. |
| 2010/0324353 A1 | 12/2010 | Helle |
| 2011/0013818 A1 | 1/2011 | Eriksson Järliden |
| 2011/0206252 A1 | 8/2011 | Eriksson Järliden |
| 2012/0108882 A1 | 5/2012 | Hoedl |
| 2012/0165957 A1 | 6/2012 | Everland et al. |
| 2013/0102832 A1 | 4/2013 | Hoedl et al. |
| 2013/0102891 A1 | 4/2013 | Binnekamp et al. |
| 2013/0131434 A1 | 5/2013 | Nakaji et al. |
| 2013/0338423 A1 | 12/2013 | Nakaji et al. |
| 2014/0275715 A1 | 9/2014 | Brachman et al. |
| 2014/0296612 A1 | 10/2014 | Schwartz |
| 2014/0316187 A1 | 10/2014 | Nakaji et al. |
| 2015/0057487 A1 | 2/2015 | Nakaji et al. |
| 2015/0140535 A1 | 5/2015 | Geri et al. |
| 2015/0196778 A1 | 7/2015 | Nakaji et al. |
| 2015/0321024 A1 | 11/2015 | Nakaji et al. |
| 2015/0367144 A1 | 12/2015 | Flynn et al. |
| 2016/0242855 A1 | 8/2016 | Fichtinger et al. |
| 2017/0021191 A1 | 1/2017 | Brachman et al. |
| 2017/0120073 A1 | 5/2017 | Brachman et al. |
| 2017/0215824 A1 | 8/2017 | Brachman et al. |
| 2017/0252575 A1 | 9/2017 | Nakaji et al. |
| 2020/0047001 A1 | 2/2020 | Nakaji et al. |

FOREIGN PATENT DOCUMENTS

| | | |
|---|---|---|
| CA | 2834559 | 11/2018 |
| CA | 3017174 | 1/2020 |
| DE | 613 528 | 5/1935 |
| EP | 0 292 630 B1 | 8/1995 |
| EP | 0 906 769 A2 | 4/1999 |
| EP | 2701803 B1 | 8/2018 |
| EP | 3456384 | 3/2019 |
| JP | S52-9424 | 7/1975 |
| JP | H09-028810 | 4/1997 |
| JP | 2001-266903 | 9/2001 |
| JP | 3095304 | 7/2003 |
| JP | 2007-512112 | 5/2007 |
| JP | 2009-515603 | 4/2009 |
| JP | 2010-536529 | 12/2010 |
| JP | 6365983 | 7/2018 |
| WO | WO 2007/106531 A1 | 9/2007 |
| WO | WO 2012/100206 A2 | 7/2012 |
| WO | WO 2012/149580 A1 | 11/2012 |
| WO | WO 2016/171961 | 10/2016 |
| WO | WO 2016/179420 | 11/2016 |

OTHER PUBLICATIONS

International Search Report; International Application No. PCT/US2012/035907, dated Sep. 26, 2012; 3 pages.

International Search Report; International Application No. PCT/US2012/035909, dated Aug. 30, 2012; 3 pages.

Crepeau, R.H., et al., "Image Processing of Imperfect Protein Arrays: Sectioned Crystals and Tubulin Sheets and Rings". Elec. Microsc. Soc. Amer. Proc. 40:84-87, 1982.

Crepeau, R.H., et al., "Reconstruction of imperfectly ordered zinc-induced tubulin sheets using cross-correlation and real space averaging". Ultramicroscopy, 6, 7-18, 1981.

(56) References Cited

OTHER PUBLICATIONS

Dagnew, E., et al., "Management of newly diagnosed single brain metastasis using resection and permanent iodine-125 seeds without initial whole-brain radiotherapy: a two institution experience". Neurosurg Focus. 15; 22(3):E3, 2007.
Delaney, T.F., et al., "Intraoperative dural irradiation by customized 192I iridium and 90 Yttrium brachytherapy plaques". Int. J. Radiat Oncol Biol Phys. 57(1): 239-245, 2003.
Ewersten, et al., "Biopsy Guided by Real-Time Sonography Fused with MRI: A Phantom Study", American Journal of Roentgenology. 2008; 190: 1672-1674. 10.2214/AJR.07.2587.
Gutin, P.H., et al., "A coaxial catheter system for afterloading radioactive sources for the interstitial irradiation of brain tumors. Technical note". J. Neurosurg 56: 734-735, 1982.
Gutin, P.H., et al., "Brachytherapy of recurrent tumors of the skull base and spine with iodine-125 sources". Neurosurgery 20:938-945, 1987.
Hamilton, A.J., et al., "The use of gold foil wrapping for radiation protection of the spinal cord for recurrent tumor therapy". Int. J. Radiat Oncol Biol Phys. 32(2):507-511, 1995.
Hilaris, B.S., et al., "Interstitial irradiation for unresectable carcinoma of the lung". Ann Thoracic Surg; 20:491-500, 1975.
Hilaris, B.S., et al., "Intraoperative radiotherapy in stage I and II lung cancer". Semin Surg Oncol. 3:22-32, 1987.
Huang, K., et al., "Surgical resection and permanent iodine-125 brachytherapy for brain metastases". J. Neurooncol. 91:83-93, 2009.
Jenkins, H.P., et al., "Clinical and experimental observations on the use of a gelatin sponge or foam". Surg 20:124-132, 1946.
Kneschaurek, P. et al.: "Die Flabmethode Zur Intraoperativen Bestrahlung. Öthe Flab-Method for Intraoperative Radiation Therapy", Strahlentherapie und Oknologie, Urban Und Vogel, Muenchen, DE, vol. 171, No. 2; Feb. 1, 1995, pp. 61-69, XP000610565, ISSN:0179-7158.
Marchese, M.J., et al., "A versatile permanent planar implant technique utilizing iodine-125 seeds imbedded in gelfoam". Int J Radiat Oncol Biol Phys 10:747-751, 1984.
Murphy, M.K., et al., "Evaluation of the new cesium-131 seed for use in low-energy x-ray brachytherapy". Med Phy 31(6): 1529-1538, Jun. 2004.
Nori, D., et al., "Intraoperative brachytherapy using Gelfoam radioactive plaque implants for resected stage III non-small-cell lung cancer with positive margin: A pilot study". J Surg Oncol. 60:257-261, 1995.
Parashar, B., et al., "Cesium-131 permanent seed brachytherapy: Dosimetric evaluation and radiation exposure to surgeons, radiation oncologists, and staff". Brachytherapy. 10:508-511, 2011.
Patel, S., et al., "Permanent iodine-125 interstitial implants for the treatment of recurrent Glioblastoma Multiforme". Neurosurgery 46 (5) 1123-1128, 2000.
Rivard, M.J., "Brachytherapy dosimetry parameters calculated for a 131 Cs source". Med Phys. 34(2): 754-765, 2007.
Rogers, C.L., et al., "Surgery and permanent 125-I seed paraspinal brachytherapy for malignant tumors with spinal cord compression". Int. J. Radial Oncol Biol Phys. 54(2): 505-513, 2002.
Wernicke, A.G., et al., "Feasibility and safety of Gliasite brachytherapy in the treatment of CNS tumors following neurosurgical resection". J. Cancer Res Ther. 6(1), 65-74, Jan.-Mar. 2010.
CivaSheet; "Precision Therapy Without the Beam"; CivaTech Oncology Inc.; CivaTech; https://civatechoncology.com/professionals/civasheet/2 pages; Accessed on Oct. 2018.
CivaSheet; "Precision Therapy Without the Beam"; CivaTech Oncology Inc.; CivaTech; https://civatechoncology.com/products-2/products/; 5 pages; Accessed on Oct. 2018.
Aima, Manik et al.; "Dosimetric Characterization of a New Directional Low-Dose Rate Brachytherapy Source"; Department of Medical Physics; Mar. 11, 2018; 32 pages.
Rivard, Mark J.; "A Directional Pd Brachytherapy Device: Dosimetric Characterization and Practical Aspects for Clinical Use"; Department of Radiation Oncology; Brachytherapy 16 (2017) pp. 421-432.
Office Action dated Apr. 2, 2015; European Patent Application No. 12724426.7; 5 pages.
Office Action dated Oct. 30, 2015; European Patent Application No. 12724426.7; 4 pages.
Office Action dated Feb. 9, 2016; Japanese Application No. 2014-508190; 7 pages including english translation.
International Search Report; International Application No. PCT/US2016/031035; filed May 5, 2016; 15 pages; dated Aug. 5, 2016.
International Search Report and Written Opinion; International Application No. PCT/US2016/027143, filed Apr. 12, 2016; dated Aug. 25, 2016; 7 pages.
Decision of Rejection dated Feb. 4, 2016, Japanese Patent Application No. 2014-508190 with English Translation; 4 pages.
Search and Examination Report; Application No. P1140/13; Filed on Oct. 24, 2013 (PCT Apr. 30, 2012); 10 pages.
Summons to Attend Oral Proceedings dated Aug. 18, 2017; European Application No. 12724426.7; 5 pages.
Office Action dated Nov. 2, 2017; European Patent Application No. 12724427.5; 4 pages.
Extended European Search Report; Application No. 18186392.9; dated Jan. 7, 2019; 7 pages.
Miller, S., et al., "Advances in the virtual reality interstitial brachytherapy system." Engineering Solutions for the Next Millenium. 1999 IEEE Canadian Conference on Electrical and Computer Engineering (Cat. No. 99TH8411). vol. 1. IEEE, 1999.

\* cited by examiner

RADIOACTIVE SEED LOADING APPARATUS

FIELD

The invention generally relates to improvements to radioactive brachytherapy.

BACKGROUND

Tumors in living organisms are highly variable in size, location and their amount of infiltration into normal tissues, and the variability of tumors in general make them very difficult to treat with a one-size fits all approach. Furthermore, the extent of tumors and/or void created upon debulking are typically not known until presented in the operating room. Thus, the options necessary to effectively treat a tumor or tumor bed need to be quite diverse.

Brachytherapy involves placing a radiation source either into or immediately adjacent to a tumor. It provides an effective treatment of cancers of many body sites. Brachytherapy, as a component of multimodality cancer care, provides cost-effective treatment. Brachytherapy may be intracavitary, such as when treating gynecologic malignancies; intraluminal, such as when treating esophageal or lung cancers; external surface, such as when treating cancers of the skin, or interstitial, such as when treating various central nervous system tumors as well as extracranial tumors of the head and neck, lung, soft tissue, gynecologic sites, liver, prostate, and skin.

SUMMARY

The systems, methods, and devices described herein each have several aspects, no single one of which is solely responsible for its desirable attributes. Without limiting the scope of this disclosure, several non-limiting features will now be described briefly.

In one embodiment, a loading apparatus comprises a base having a loading bed configured to support a radioactive seed carrier configured to receive one or more radioactive seed, and a base loading channel configured to receive an injection device, the injection device configured to inject the radioactive seed into the radioactive seed carrier, The loading apparatus may comprise a lid configured to engage with the base to create a loading chamber with the loading bed as the lower surface, the lid having a spring-loaded push block configured to exert force towards the loading bed of the base, wherein when a radioactive seed carrier is positioned on the loading bed the spring-loaded push block secures the radioactive seed carrier.

In some embodiments, the loading apparatus further comprises a lid loading channel substantially co-axial with the base loading channel when the lid is engaged with the base.

In some embodiments, the loading apparatus further comprises one or more seed alignment windows positioned to provide visibility into the loading chamber where one or more of the radioactive seeds are positioned in the radioactive seed carrier.

In some embodiments, the loading apparatus further comprises one or more carrier alignment windows positioned to provide visibility into the loading chamber where the radioactive seed carrier is positioned.

BRIEF DESCRIPTION OF THE DRAWINGS

The principles of the present invention will be apparent with reference to the following drawings, in which like reference numerals denote like components:

FIG. 9A is a top view of a loader, with FIG. 9B illustrating a cross-section 9B of FIG. 9A and FIG. 9C illustrating cross section 9C of FIG. 9A.

DETAILED DESCRIPTION

Although certain preferred embodiments and examples are disclosed below, inventive subject matter extends beyond the specifically disclosed embodiments to other alternative embodiments and/or uses and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Terms

In order to facilitate an understanding of the systems and methods discussed herein, a number of terms are described below. The terms described below, as well as other terms used herein, should be construed to include the provided descriptions, the ordinary and customary meaning of the terms, and/or any other implied meaning for the respective terms. Thus, the descriptions below do not limit the meaning of these terms, but only provide exemplary descriptions.

Tumor: an abnormal growth of tissue resulting from uncontrolled, progressive multiplication of cells. Tumors can be benign or malignant.

Tumor bed: an anatomical area of a patient (e.g., a human or other mammal) where a tumor exists (pre-operative tumor bed) and/or an area surrounding a surgically removed tumor (post-operative tumor bed), such as a cranial cavity from which a tumor was surgically removed. Even after surgical removal of a tumor, the remaining tumor bed of the patient may include tumor cells.

Treatment area: an anatomical area that is targeted for delivery of radiation, such as from one or more radiation delivery devices (e.g., the carriers discussed below). A treatment area may include tissue below and/or around a location where the radiation deliver device is positioned, such as an anatomical area of a tumor or a tumor bed.

Treatment surface: an anatomical surface of a patient where a radiation delivery device is to be placed to deliver radiation to a treatment area, such as the treatment surface itself and/or tissue below the treatment surface. A treatment surface may be a portion of a tumor bed or any other anatomical surface. For example, if a tumor bed is surgically created, the treatment surface may include an entire exposed surface of the tumor bed, a portion of such exposed surface, or the entire exposed surface of the tumor bed as well as a surrounding area of tissue.

Brachytherapy: radiation treatment in which the radiation delivery device is placed directly on and/or close to a treatment surface of the body, such as directly on the surface of the body, within the body, or in a tumor bed. For example, brachytherapy may be intracavitary, such as in cranial or gynecologic malignancies; intraluminal, such as in esophageal or lung cancers; external, such as in cancers of the skin; and/or interstitial, such as in treatment of various central nervous system tumors as well as extracranial tumors of the head, neck, lung, soft tissue, gynecologic sites, rectum, liver, prostate, and penis.

Seed: a radioactive material that is configured for delivery of radiation to a tumor and/or tumor bed. A seed may be in various shapes and sizes, such as cylinder, cone, sphere, pyramid, cube, prism, rectangular prism, triangular prism, and/or any combination of these or other shapes. While seeds are generally referred to herein as cylindrical, any other shape or size of seed may alternatively be used in the various systems and methods discussed herein. Seeds may comprise any combination of one or more of multiple radioactive components, such as Cs 131, Ir 192, I 125, Pd 103, for example. Seeds may include a protective outer shell that partially or fully encases the radioactive material. Seeds are one form of radiation source. The term "radiation source," as used herein, generally refers to a radioactive seed (or other object that emits radiation), either alone (e.g., a seed) or embedded, or otherwise attached to, a carrier (e.g., a tile carrier with an embedded radioactive seed).

Carrier (also referred to as a "carrier sheet"): a substrate that holds or contains a radioactive seed. A carrier that contains one or more seeds is a radiation delivery device. Carriers may comprise various materials, such as one or more biocompatible materials including collagen. Carriers may be configured for permanent implantation into a tumor bed, such as to provide radioactive energy to a treatment surface surrounding an area where a tumor has been removed in order to treat any remaining malignant tissue. Carriers can be composed of various materials and take on various shapes and sizes. Examples carriers, such as carriers having various sizes, shapes, configurations, etc., are included in the following patent and patent application, each of which is hereby incorporated by reference in its entirety and for all purposes:

U.S. patent application Ser. No. 14/322,785, filed Jul. 2, 2014, now U.S. Pat. No. 8,876,684, entitled "Dosimetrically Customizable Brachytherapy Carriers and Methods Thereof In The Treatment Of Tumors," and U.S. patent application Ser. No. 14/216,723, filed Mar. 17, 2014, publication No. 2014/0275715, entitled "Dosimetrically Customizable Brachytherapy Carriers and Methods Thereof In The Treatment Of Tumors."

Tile Carrier (also referred to as "Tile"): type of carrier that is substantially planar and generally maintains a two-dimensional planar geometry when placed in a tumor bed. Depending on the material of the tile, though, the tile may be malleable such that the tile can be deformed by bending in order to better conform to a tumor bed. For example, for tiles comprising essentially collagen (and/or other malleable materials), the tiles may be substantially bent as placed in or on a treatment surface (and/or when pressed against the treatment surface) to conform with the shape of the treatment surface, such as a post-operative tumor bed.

Gore Carrier (also referred to as "Gore"): type of carrier that is 3-dimensional and conforms to the tumor bed while maintaining the geometry necessary for an effective implant. In some embodiments, gores are initially planar and are reconfigured to take on a 3-dimensional shape, such as to form a hemispherical surface that may be placed into a similarly shaped tumor cavity.

Star Carrier (also referred to as "Star" or "arm-based carrier"): type of carrier that assumes a conformable 3-dimensional shape when arranged and placed into an operative cavity or similar space and conforms to the treatment environment while maintaining the geometry necessary for an effective implant. However, in some embodiments, Star carriers may be used in their initial planar state to cover a relatively flat tumor or tumor bed area.

Loader (also referred to as a "loading device" or "loading apparatus"): a device that aids in placement of radioactive seeds in carriers, such as via injection of seeds into carriers. A loader may include multiple components, such as to hold a carrier in place and guide a delivery device (e.g., a needle or injector) into the carrier in order to place a seed at a precise location in the carrier. U.S. patent application Ser. No. 13/460,809, filed Apr. 30, 2012, now U.S. Pat. No. 8,939,881, entitled "Apparatus For Loading Dosimetrically Customizable Brachytherapy Carriers," and U.S. patent application Ser. No. 14/696,293, filed Apr. 24, 2015, entitled "Apparatus and Method for Loading Radioactive Seeds Into Carriers," which are each hereby incorporated by reference in their entirety for all purposes, describe several embodiments of loaders. As discussed further herein, loaders may be operated manually, such as by human operators, or may be fully automated, such that carriers can be loaded with seeds using an automated process. Alternatively, loaders may be configured to be automated in part and require manual operation in part.

Example Carriers

Figure 1A:
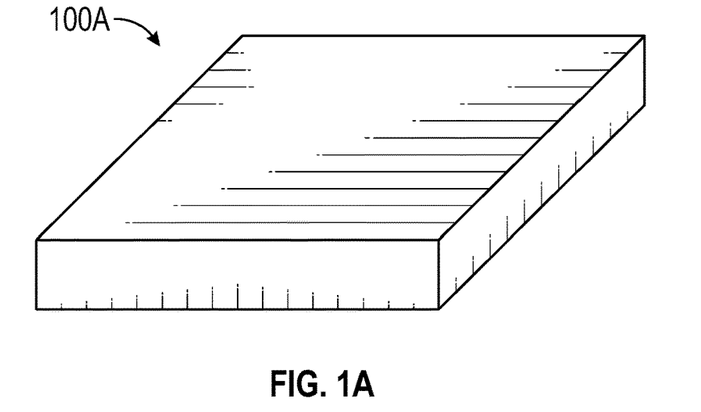
FIGS. 1A and 1B are perspective views of an example carrier in a "cold" carrier state and a "hot" carrier state, respectively.
Figure 1B:
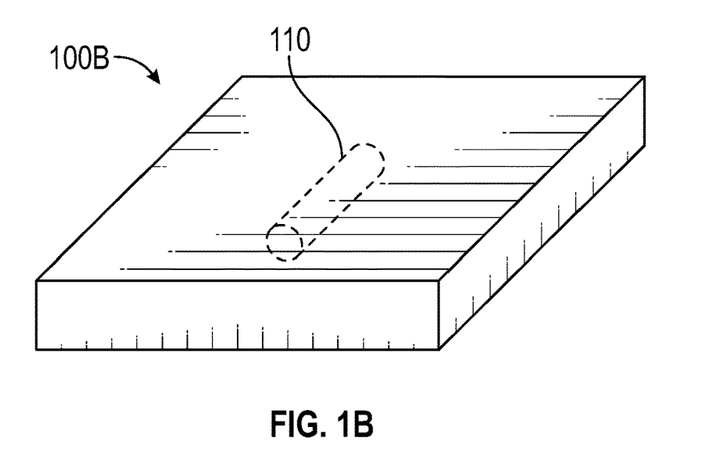

FIGS. 1A and 1B are perspective views of an example carrier 100 in a "cold" carrier 100A state and a "hot" carrier 100B state. As noted above, carriers may be available in various shapes, sizes, and configurations. The example carrier 100 is a "tile" carrier that is generally square in shape (e.g., substantially the same width and length), with a much smaller height. For example, the width and length of the carrier 100 may be orders of magnitude larger than the height of the carrier, such as a factor of 200 to 1,000. In one example, the width and length of the carrier 100 are about 1 cm, and the height of the carrier 100 is about 1 mm-8 mm. In other embodiments, carriers may have other sizes, configurations, materials, etc.

Carrier 100A is considered a "cold" carrier because it has not yet been loaded with a radioactive seed. Carrier 100B is considered a "hot" carrier because it has a radioactive seed 110 embedded within it. As discussed in the related patents and patent applications noted above, the radioactive seeds can have various shapes, sizes, and characteristics. In the examples discussed herein, radioactive seeds are illustrated as generally cylindrical, such as the cylindrical seed 110. However, other shapes and sizes of seeds may be used in other implementations. In the examples discussed herein, radioactive seeds are substantially rigid, such that they maintain their shape within their respective carriers. In other embodiments, seeds may be more pliable, such that they are somewhat malleable in taking on a shape of a specific treatment surface.

Carriers may comprise various materials, such as one or more biocompatible materials including collagen. Carriers may be configured for permanent implantation into a tumor bed, such as to provide radioactive energy to a treatment surface surrounding an area where a tumor has been removed in order to treat any remaining malignant tissue. Carriers can be composed of various materials and take on various shapes and sizes.

Figure 2:
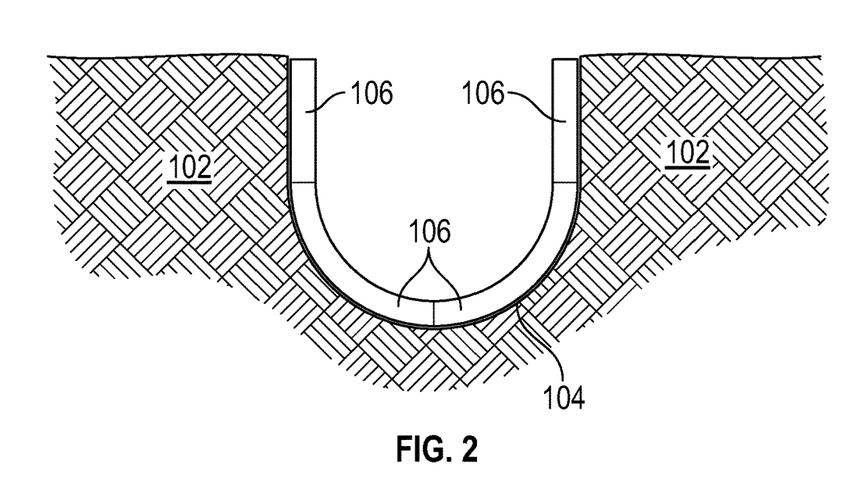
FIG. 2 is a cross-sectional drawing illustrating a portion of patient tissue having a tumor bed therein.

FIG. 2 is a cross-sectional drawing illustrating a portion of patient tissue 102 having a tumor bed 104 therein. The tumor bed 104 may have been created by a surgical process, such as a tumor debulking process that removed tumor cells. For example, the tissue 102 may represent cranial tissue of a human (or other mammal) wherein the tumor bed 104 is surgically created in order to remove one or more tumors from the brain (and/or surrounding areas) of the patient. Thus, the tissue 102 may represent different types of material, such as bone, fatty tissue, brain tissue, etc. Any reference herein to "tissue" may reference to any type of mammalian material, including bone, fatty tissue, brain tissue, etc.

In the example of FIG. 2, four tile carriers 106 (e.g., such as the hot carrier 100B) are illustrated as already placed within the tumor bed 104, and radiation is delivered to the treatment area by the radioactive seeds within the carriers 106. Placement of the tiles 106 in the tumor bed 104 may occur in the surgical room, such as immediately after a surgical procedure, or elsewhere at some time after the surgical procedure, such as in a separate procedure performed hours, days, or weeks later. In the embodiment of FIG. 2, the tiles 106 are pliable such that they conform to the treatment surface, which is the non-planar outer surface of the tumor bed 104 in this example. In one embodiment, the tiles 106 may comprise collagen that provides such flexibility in conforming the tiles 106 to a nonplanar surface.

Figure 3:
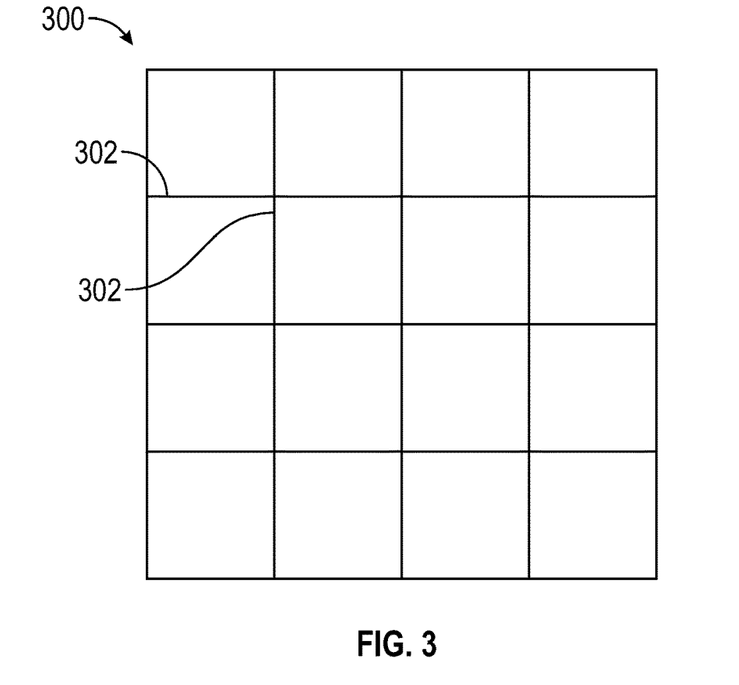
FIG. 3 is a top view of a carrier sheet configured for implantation of multiple radioactive seeds.

FIG. 3 is a top view of a carrier sheet 300 configured for implantation of multiple radioactive seeds. The example carrier sheet of 300 may be, for example, a 4 cm×4 cm carrier sheet configured for trimming at each centimeter to create sixteen 1 cm×1 cm carriers. In some embodiments, the carrier sheet 300 may include trim lines at the locations where trimming, or cutting, of the carrier sheet should be performed, such as the trim lines 302 positioned at one centimeter intervals. A carrier sheet may be trimmed using scissors, razor blade, knife, die cutter, or similar cutting implement, to create custom sized and/or shaped carriers.

Using the trim lines in the example carrier sheet 300, a user can accurately create multiple carriers having dimensions anywhere between 1 cm-4 cm on either side. For example, a user could create four 1 cm×4 cm carriers, two 2 cm×4 cm carriers, or sixteen 1 cm×1 cm carriers using the trim lines on carrier sheet 300. In other embodiments, trim lines may be placed at different intervals. In one embodiment, trim lines may be generated by a dosimetric planning software, such as the software discussed in U.S. patent application Ser. No. 15/017,461, entitled "Radioactive Implant Planning System and Placement Guide System," filed on Feb. 5, 2016, which is hereby incorporated by reference in its entirety. For example, in order to achieve a maximum therapeutic index, a custom shaped carrier sheet or multiple carrier sheets may be determined by software and implemented by the user. In one embodiment, the software generates a printout of the trimming pattern that can be overlaid on a carrier sheet so that the printed trimming pattern as well as the carrier sheet thereunder can be simultaneously trimmed in order to achieve the calculated carrier size, shape, pattern, etc.

Example Loading Device and Method

Figure 4A:
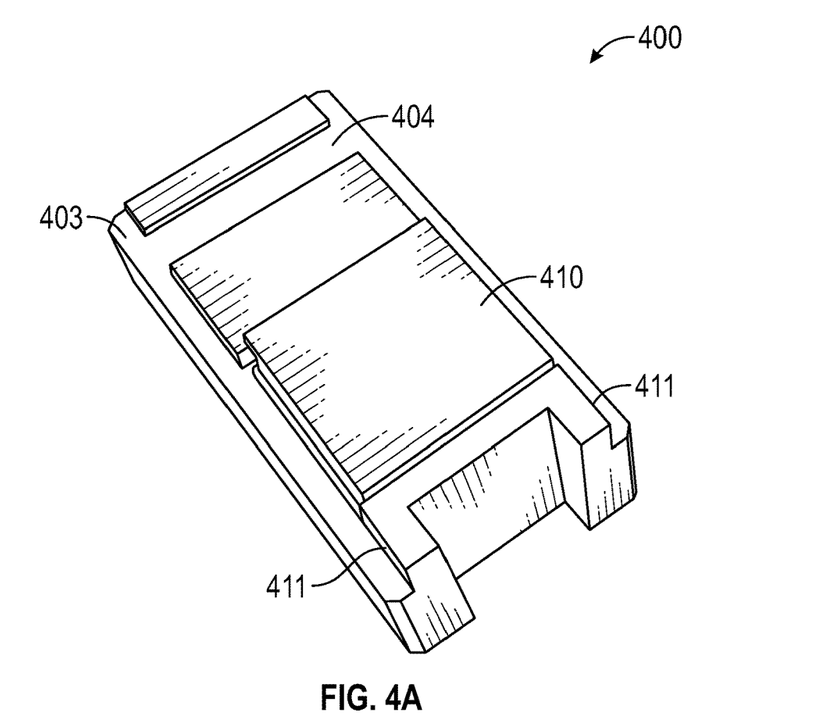
FIGS. 4A-4C are perspective views of a loading apparatus that is usable to embed radioactive seeds into carriers, while limiting exposure of the user to radioactive energy from the radioactive seeds.
Figure 4B:
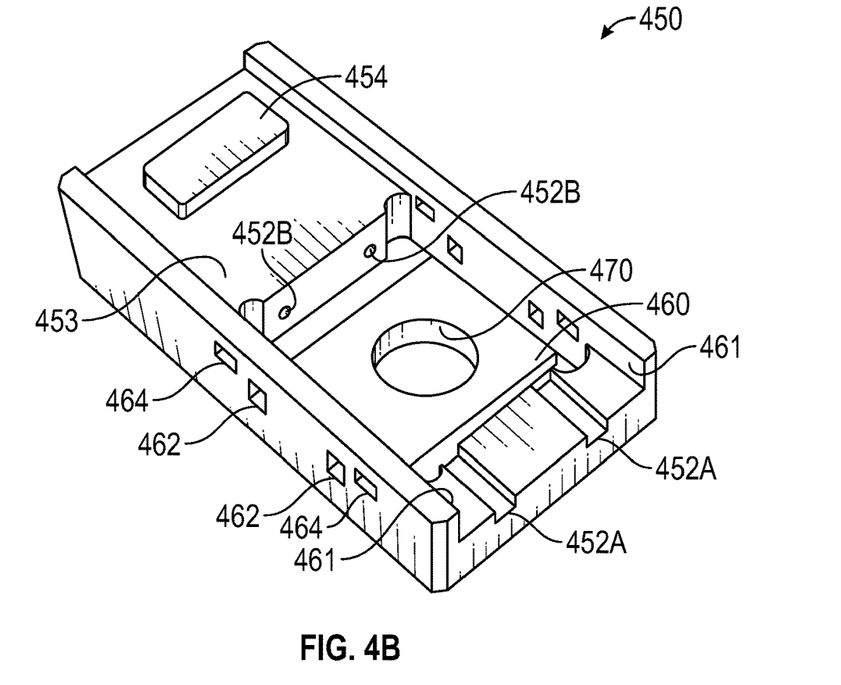
Figure 4C:
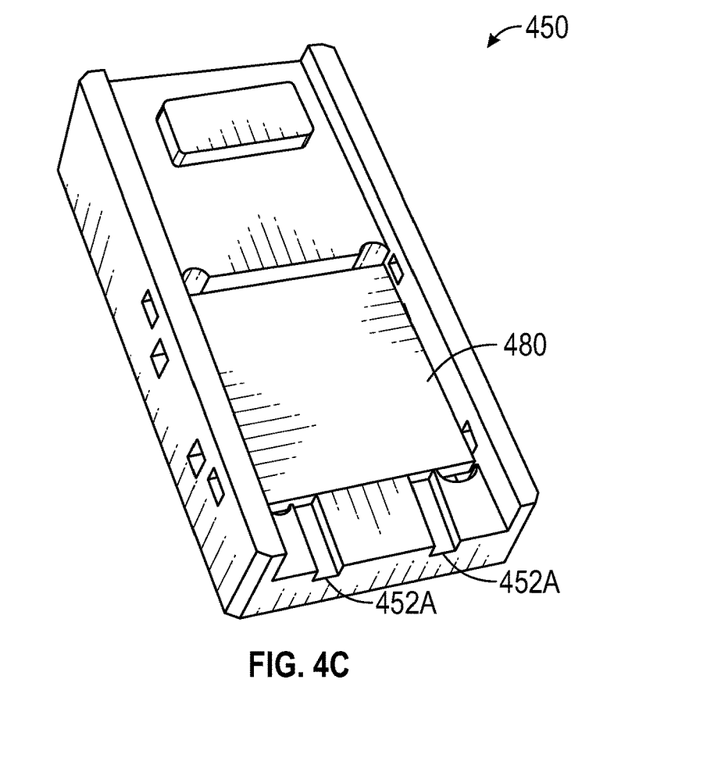

FIGS. 4A-4C are perspective views of a loading apparatus that is usable to embed radioactive seeds into carriers, while limiting exposure of the user to radioactive energy from the radioactive seeds. Advantageously, the loading apparatus facilitates accurate positioning of radioactive seeds within a carrier, as discussed in further detail below. The illustrated loaders comprise two components, a base and a lid, although in other embodiments the loaders may be separated into additional components. While specific examples of a loader are illustrated, the illustrated loaders may be modified to accommodate a wide variety of carrier dimensions and styles while still providing certain of the advantages discussed herein.

The example loaders illustrated herein are configured for facilitating embedding of radioactive seeds in conjunction with a strand of suture having one or more seeds attached thereto (e.g., seed-in-suture), such as may be inserted through the carrier using a needle, or similar insertion device. However, seeds may be inserted using the loaders discussed herein in other manners and with other insertion devices, such as to facilitate embedding of loose seeds.

In the example of FIG. 4 (including FIGS. 4A, 4B, and 4C), the loader includes a cover 400 and a base 450 configured for engagement with one another to secure a carrier sheet (or single carrier) for insertion of one or more radioactive seeds. In this example, the cover push block 410 is spring-loaded to engage with a carrier sheet positioned on a loading bed 460 of the base 450. An engagement surface 403 of the cover 400 is configured to securely engage with an engagement surface 453 of the base 450. Each of the base 450 and cover 400 have certain alignment features that allow for secure engagement of the surface of the base 450 and cover 400, which may vary from one embodiment to another embodiment of loader. In the example of FIG. 4, a protruding engagement surface 454 of the base 450 is configured to engage with a recessed engagement surface 404 of the cover 400. In other embodiments, other sizes, shapes, configurations, etc. of alignment features may be used to uniformly and securely engage the service and base of the loader.

As shown in FIG. 4C, a carrier sheet 480 is placed on the loading bed 460. With the carrier sheet 480 placed on the loading bed 460, the cover 400 may be engaged with the base 450 such that the push block 410 secures the carrier sheet 480 at a fixed position within the loader. The loader further comprises guide channels 452 configured to receive an insertion device, such as a needle threaded with a suture having multiple seeds attached thereto, and guide the insertion device through the secured carrier sheet 480 so that the seeds are properly placed within the carrier sheet 480. In the embodiment of FIG. 4, the guide channels include insertion channels 452B and exit channels 452A. Advantageously, the channels are aligned so that seeds are consistently uniformly placed within a thickness of the secured carrier sheet. While FIG. 4C illustrates a loader with two guide channels 452, in other implementations any number of guide channels may be used. For example, a loader may include from 1 to 10 (or more) guide channels.

The loader of FIG. 4 includes additional features that will be discussed further with reference to other figures. For example, the base 450 includes seed alignment windows 462 positioned so that, particularly when a user reinserts a carrier with a strand of seeds already embedded at 90° from the original loading direction (used for insertion of the strand of seeds), the user can view position of the strand of seeds within the carrier positioned within the loader. For example, in some embodiments, when a strand is positioned properly (e.g., seeds are positioned in a central portion of individual carriers that will be separated after seed implantation is completed), seeds should be viewable in one or both of the alignment windows 462 (e.g., through a portion of a collagen carrier). In other embodiments, other alignment window configurations are possible, such as use of a single alignment window or additional alignment windows. Example base 450 also includes carrier alignment windows 464, which are usable to ensure that the carrier sheet is properly seated on the loading bed 460, such as by confirming that each of the four corners of the carrier are visible in the four alignment windows 464 of base 450.

Figure 5A:
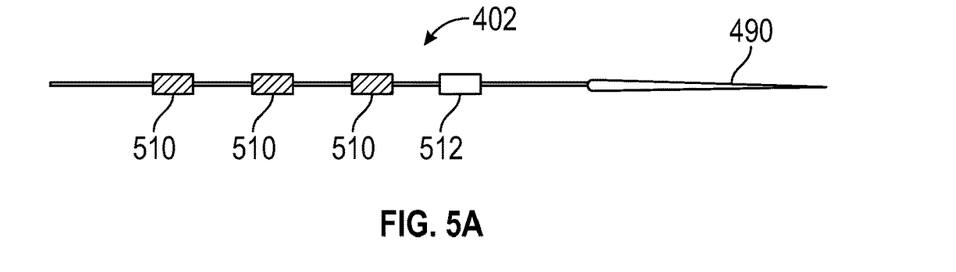
FIGS. 5A and 5B illustrates example strands that may be used, in conjunction with an insertion device, with the loaders discussed herein.
Figure 5B:
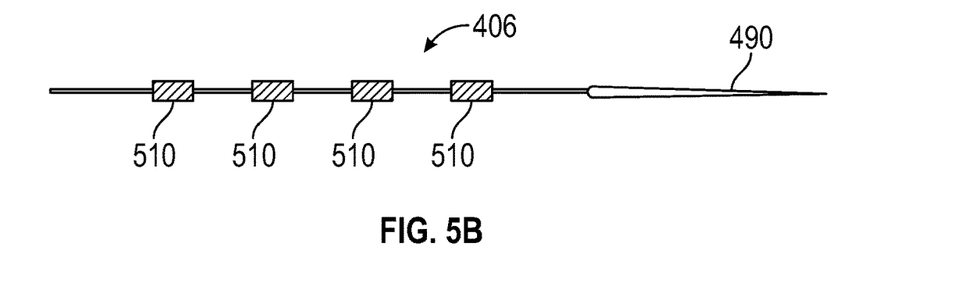

FIGS. 5A and 5B illustrate example strands 402 and 406 that may be used, in conjunction with an insertion device 490, with the loaders discussed herein. Each of the strands 402 and 406 include multiple radioactive seeds 510 attached to the strand (e.g. suture or other durable material). The strand 402 includes a dummy seed 512 that is sized and shaped similar to a radioactive seed 510, but is not radioactive itself. In other embodiments, a dummy seed may be simply a colored marker on the strand, rather than a structure size and shaped similar to a radioactive seed. In some embodiments, a dummy seed 512 may be used to determine when each of the radioactive seeds 510 are properly placed within a carrier sheet. In the embodiment of FIG. 5, the insertion device 490 is a needle, but other insertion devices may also be used.

Figure 6:
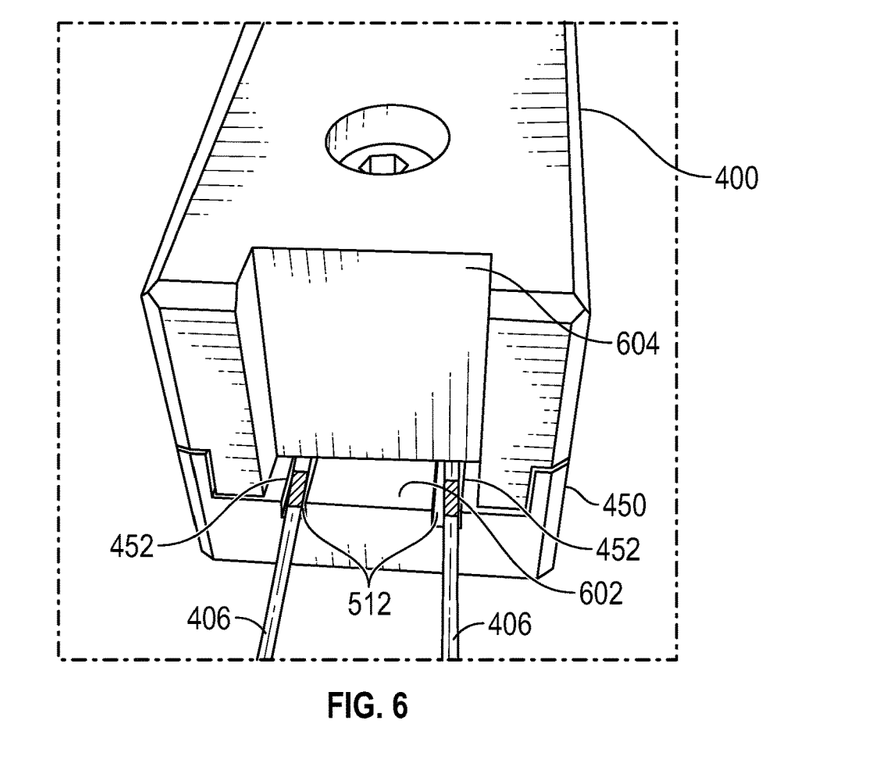
FIG. 6 is a perspective view of an insertion side of a loader, comprising a base engaged with a cover, and shown with a strand inserted through the guide channels.

Moving to FIG. 6, a perspective view of an insertion side of a loader, comprising base 450 engaged with cover 400, is shown with strands 406 inserted through each of the guide channels 452. In this example, dummy seeds 512 are shown positioned with reference to the cover 400 to indicate that the strand, and the corresponding radioactive seeds on the strand, are properly positioned within the carrier sheet. In particular, the strand in this example is configured so that when the dummy seeds 512 are aligned with an alignment base 602, the user may determine that the radioactive seeds are properly positioned within the one or more individual carriers of a carrier sheet within the loader. In this example, the cover 400 is manufactured to include a recess 604 that defines the alignment base 602 allows when the cover 400 and base 450 are engaged, and that allows visibility of strands entering the guide channels 452 across the alignment base 602.

In some implementations, a needle longer than the loader may be used and pulled through the loading channels. Once the needle protrudes from the loader, it may be pulled the rest of the way with clamps, needle-nose plier, or another tool (such as an automated robotic tool). For example, if a loader length is 10 cm, an 11 cm (or longer) needle may be used to feed the strand through the loading channels and embed the seeds within the carrier sheet.

Figure 7A:
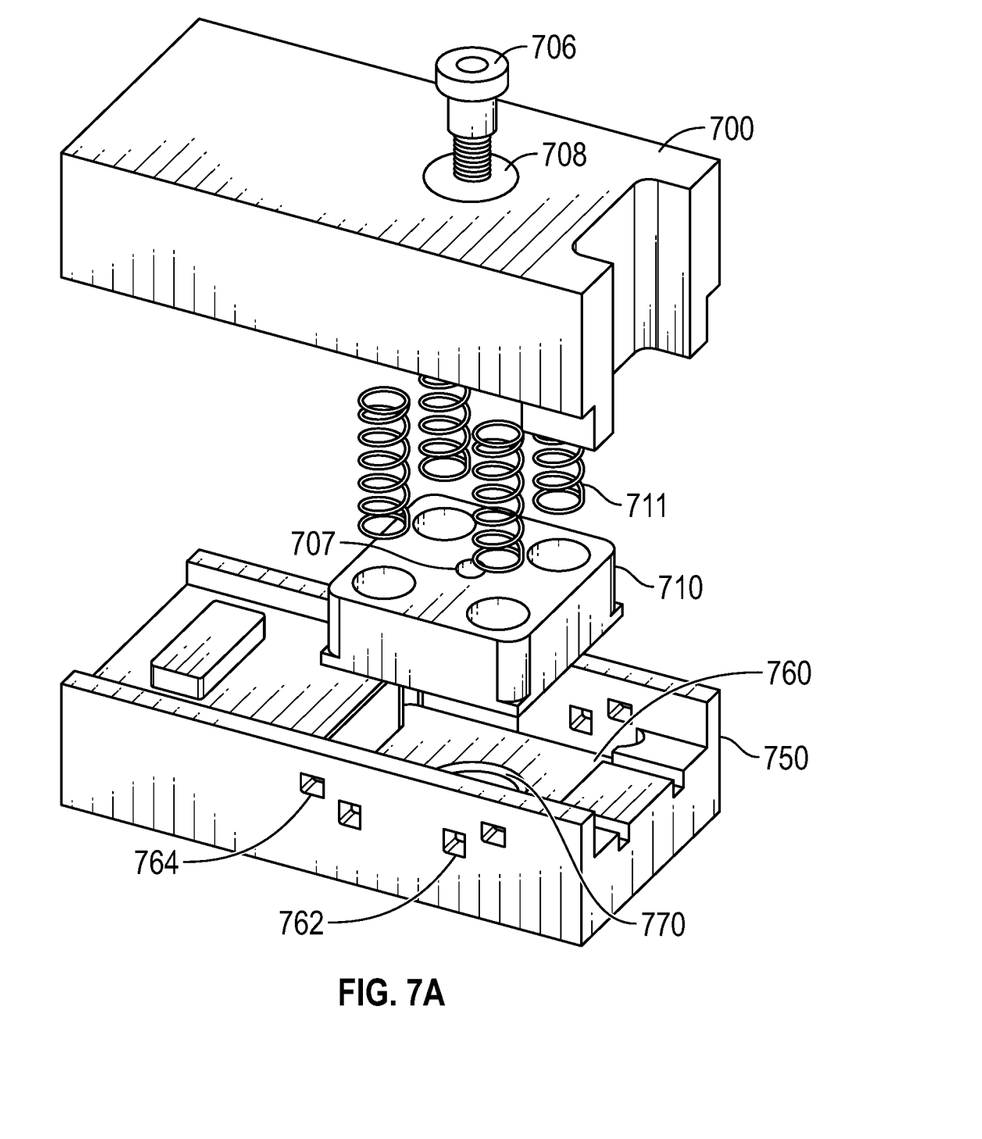
FIGS. 7A and 7B illustrate exploded views of a loader, each including a cover, a base, and push block.
Figure 7B:
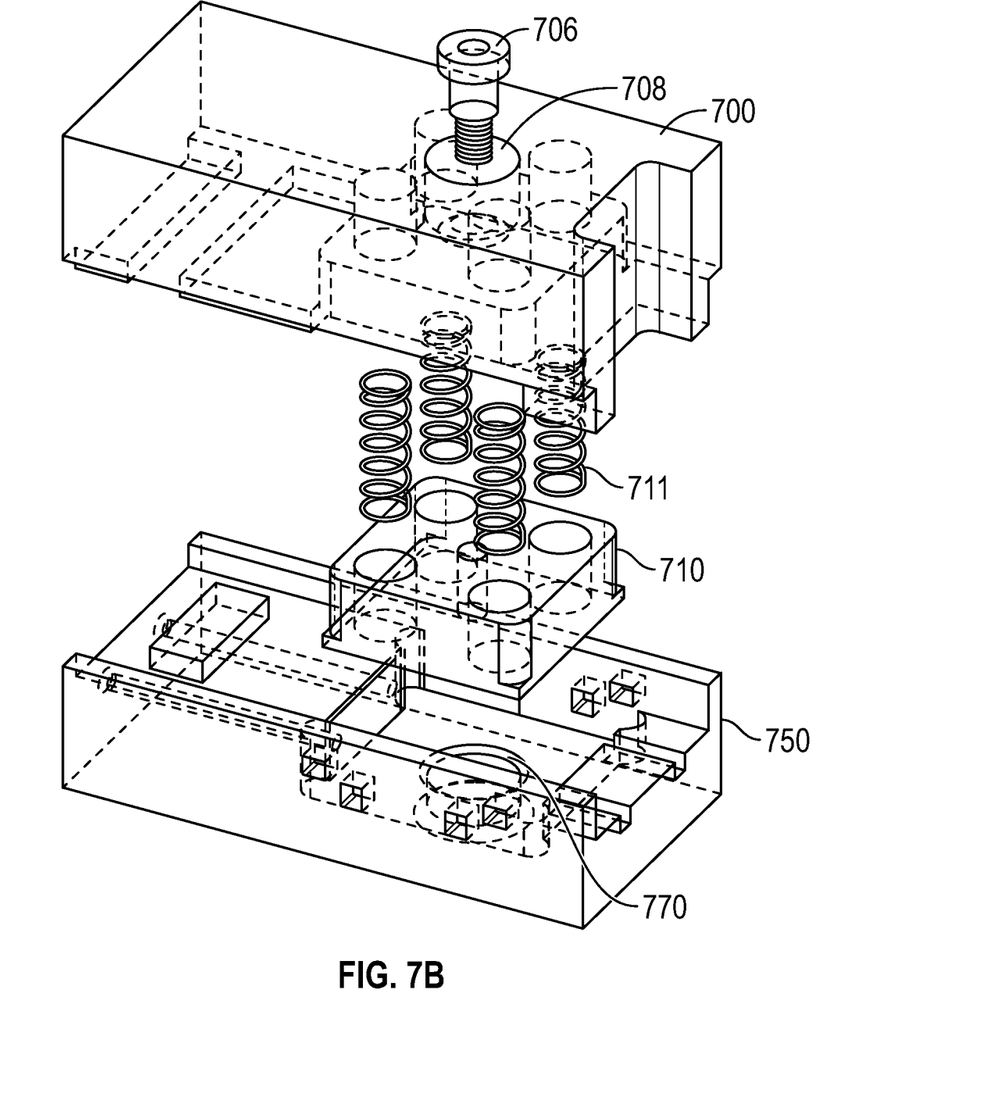

FIGS. 7A and 7B are exploded views of a loader, each including a cover 700, a base 750, and push block 710. FIG. 7B includes broken lines illustrating portions of the loader not viewable from the perspective view shown in FIG. 7A. In this embodiment, a shoulder screw 706 threadedly engages with threaded recess 707. The shoulders screw 706 maintains attachment of the push block 710 with the cover 700, so that the springs 711 are substantially retained within the push block 710. The push block 710 maintains mobility by virtue of a movement channel 708 that allows the shoulder screw 706 to move up and down within the channel 708 as the push block 710 is moved up and down.

Also visible in FIG. 7 is an access port 770 through a bottom surface of the base 750. In some embodiments, the access port 770 is usable for removal of a carrier sheet from the loader. For example, a push rod, screwdriver, tweezers, etc. may be inserted into the aperture 770 to push the carrier sheet off the loading bed surface, allowing easy removal of the carrier sheet from the loader. In some embodiments, a bidirectional plunger, or other mechanical structure may be attached to the base 750 around the aperture 770 for the same purpose, while retaining attachment to the base 750.

Figure 8A:
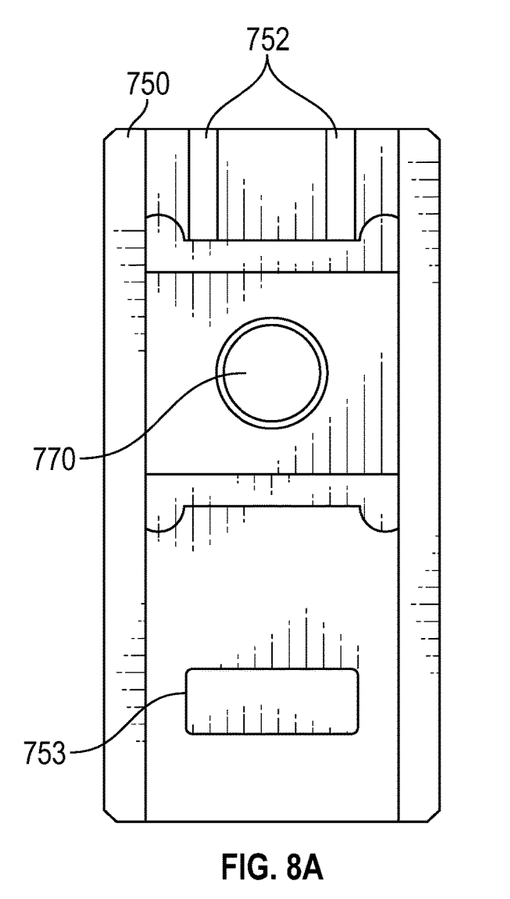
FIG. 8A illustrates engagement surfaces of a base.
Figure 8B:
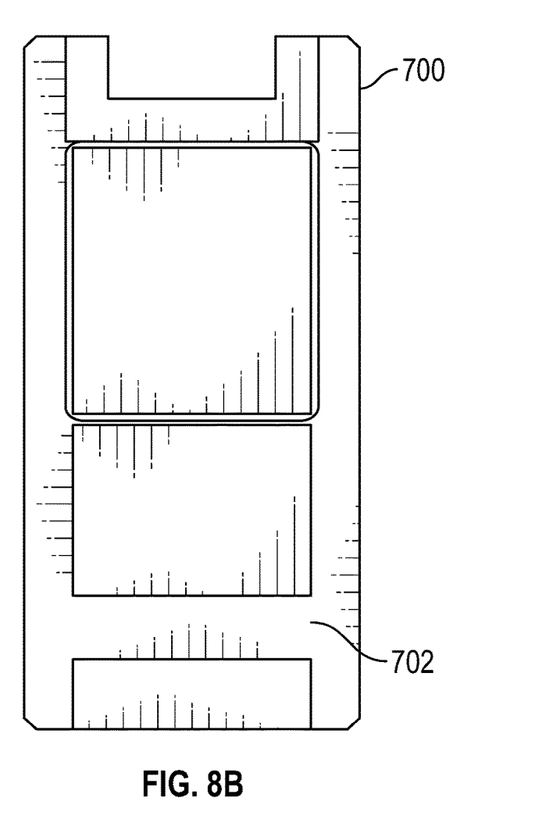
FIG. 8B illustrates engagement surfaces of a cover.

FIG. 8A illustrates engagement surfaces of the base 750 and cover 700. As shown in FIG. 8B, which illustrates the cover 700, the engagement surface 702 of the cover 700 is configured to securely engage with an engagement surface 753 of the base 750 shown in FIG. 8B. Also viewable in FIG. 8A is the access port 770 through which a tool may be inserted to remove a carrier sheet. In this embodiment, loading channels 752 are part of the base 750, but in other embodiments the loading channels may be entirely or partially part of the cover 700.

Figure 9A:
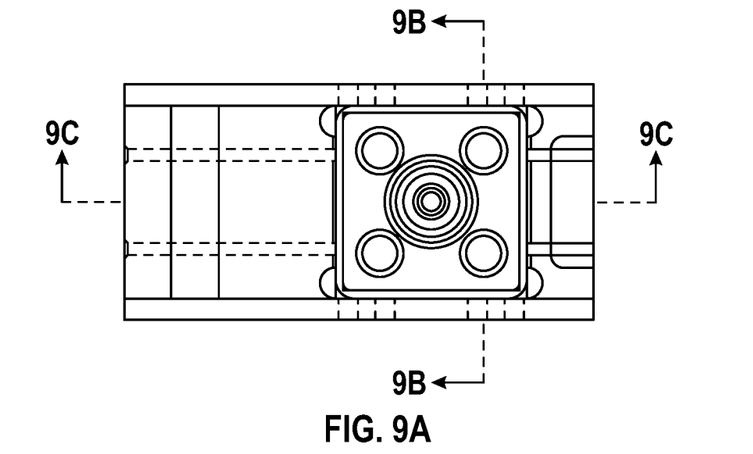
Figure 9B:
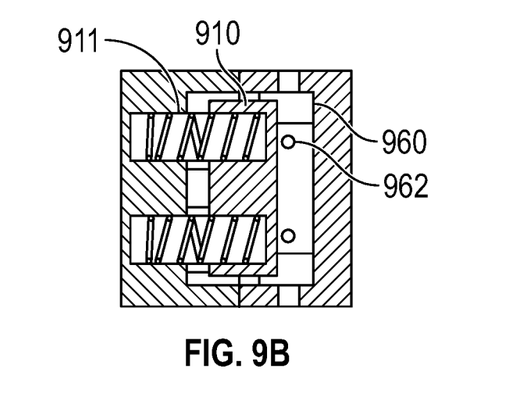
Figure 9C:
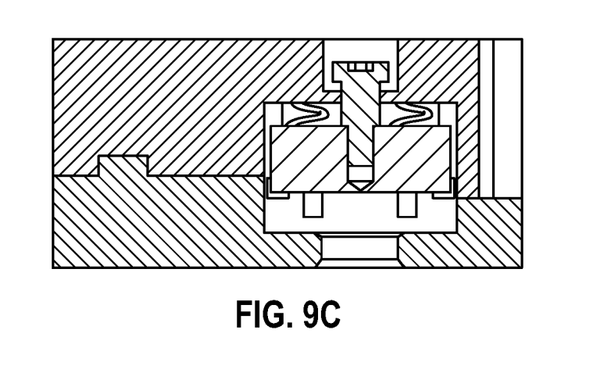

FIG. 9A is a top view of a loader, with FIG. 9B illustrating a cross-section 9B of FIG. 9A and FIG. 9C illustrating cross section 9C of FIG. 9A. FIG. 9B illustrates the springs 911 in a compressed position and push block 910 against the loading bed 960. Loading channels 962 are shown in FIG. 9B, which are configured to receive a needle pulling a strand of seeds through the loader and into a carrier positioned on the loading bed 960.

Example Loader Variations and Options

Depending on the embodiment, a loader may be a sterilizable single or multi-use device for manual or automated loading (in real time or for pre-loading) of carriers such as but not limited to tiles, gores, or stars with radioactive seeds such as $I^{125}$, $Cs^{131}$, $Pd^{111}$, $Pd^{103}$ and/or other materials. The loaders may be constructed of metal, plastic or composite material, and manufactured by machining, casting, molding, stamping, forming or 3D printing. Embodiments of the loaders contemplated may include shielding either by way of construction with a high Z material, or with other materials with a sufficient dimension (thickness) to provide the necessary dose attenuation for a user. Other embodiments may remain unshielded, and be made of materials suitable for the purpose including but not limited to tungsten, stainless steel, nylon or plastic.

In some embodiments, an automated system may include one or more automate movement of one or both the of the main loader components, e.g., the base and cover, to automate engagement of the base on cover surface for loading of seeds. Automation of carrier sheet placement on the loading bed as well as automation of insertion of an insertion device with the string of seeds may also be performed. Such automations may be accomplished through use of hydraulic, electronic, and/or manual energy.

Example Transparent Loader Surfaces

In some embodiments, a loader may include one or more surfaces (e.g., one or more portions of the various bases, covers, push blocks, windows, etc.) composed of a transparent material, where transparency is defined to include embodiments with various levels of transparency, from fully transparent to partially transparent. In some embodiments, a level of transparency is determined or selected to provide suitable visibility to a radioactive seed position behind the transparent surface. Thus, depending on the embodiment, the level of transparency required to provide this advantage may vary. For example, if the seed location is detected by human vision, such as by a technician or surgeon that manually handles the loader and monitors position of the seed within the loader, the transparency level may be higher than if the seed location is monitored with a digital detector (e.g., a camera or sensor) that monitors and automatically detects light, whether in the visible or invisible spectrum (e.g., with object detection software executing on a computing device).

In some embodiments, the level of transparency may also be determined or selected to provide suitable shielding of radioactive energy from radioactive seeds or other sources that are placed behind the transparent surface. For example, in some embodiments the transparent material may be impregnated with lead or another material that absorbs or reflects radioactive energy. In embodiments where a human user is handling the loader, the level of radioactive shielding may be increased to reduce radiation absorbed by the user's tissue. Conversely, in a loader system where seeds are inserted into carriers using robotic components, for example, radioactive shielding requirements may be reduced.

Depending on the embodiment, the transparent loader surfaces may be formed of various materials, such as glass, plastic, etc. Such materials may allow shielding objects to be implanted within the material, such as via an injection molding process. Depending on the embodiment, shielding material may be formed above, below, or within a transparent surface of a loader in various manners. For example, in some embodiments a thin layer of high Z foil may be placed above and/or below a transparent surface, such as across an entire area of the transparent surface or a portion of the transparent surface. For example, a suitable shielding level may be obtained by use of a shielding material across the portion of a transparent surface of a loader, while still providing a suitable level of visibility beyond the transparent surface.

Overview of Certain Technical Improvements

Below are several improvements in the various loaders discussed herein. Depending on the particular loader implementation, some or all of these advantages may be present in a particular loader.

Spring loaded cover pushes and keeps the carrier sheet in place on base. For example, with reference to FIG. 7, when the cover 700 is engaged with the base 750, the push block 410 will be pushed against the loading bed 760 by the springs 711. When the carrier sheet is placed on the loading bed 760, the push block 410 exerts force on the carrier sheet so that it maintains a stable position between the push block 710 and the loading bed 760, allowing an insertion device to pass through a thickness of the carrier sheet without causing the carrier sheet to fold, buckle, or bend. Advantageously, this spring loaded cover allows carrier sheets of various thicknesses to be used in the same loader, since the force of push block 410 is not locked into a particular position.

Carrier windows allow manual or automatic (e.g., machine vision) confirmation of proper placement of a carrier sheet in the loader. For example, with reference to FIG. 4, the carrier alignment windows 464 allow a user to see within the loading bed at a height just above where the carrier sheet should be positioned to ensure that the carrier sheet is properly positioned and of the correct thickness prior to inserting the radioactive seeds. As noted above, the windows may be apertures and/or may include material that allows at least partial transparency, while possibly also provided some shielding. In some embodiments, an optical sensor may be positioned to view the carrier alignment windows and detect whether the carrier sheet is properly positioned.

Seed alignment windows allow manual or automatic (e.g., machine vision) confirmation of proper placement of seeds within the carrier sheet prior to removing the carrier sheet from the loader. For example, with reference to FIG. 4, the seed alignment windows 462 allow a user to see within the loader at the position of the carrier sheet, such as when the carrier sheet is rotated 90° and reinserted into the loader, to determine whether the radioactive seeds are properly positioned within the carrier sheet. For example, the seed alignment windows 464 may be positioned to align with a first and/or last seed when the strand is properly positioned within the carrier. As noted above, the windows may be apertures and/or may include material that allows at least partial transparency, while possibly also provided some shielding. In some embodiments, an optical sensor may be positioned to view the carrier windows and detect whether the carrier sheet is properly positioned.

Cutout of lid (or base) to view marker on strand indicating proper position of seeds in carrier. For example, as illustrated in FIG. 6, dummy seeds 512, or simply a marking 512 on the strand, may be aligned with the alignment based 602 when the strand is properly positioned. In some embodiments, a dummy seed 512 may be properly positioned when it starts to exit the loader, has just entirely exited the loader, or other known position that indicates proper placement of the seeds within the carrier sheet.

Guide channel(s) through length of base (and/or cover) for guiding needle and strand of seeds. As discussed above, the guide channels may be positioned in one or both of the base and cover depending on the embodiment. Advantageously, the guide (or "loading") channels are configured to maintain the insertion device and strand of seeds in a uniform path as it passes through the carrier sheet, such as so that each of the seeds our positioned at a central, or predetermined offset, depth of the carrier sheet. For example, in some implementations, such as according to a particular dosimetric plan, seeds are positioned closer to one surface of the carrier sheet than the other, such as 1 mm from a treatment surface of a 4 mm thick carrier sheet. Thus, the guide channels are carefully calibrated to ensure that each of the seeds is positioned at the precise offset within the carrier sheet.

Access port on base below loading bed allows carrier to be pushed out of loader. For example, FIG. 4B illustrates an access port 470 through which a tool may be inserted to push a carrier service from the loading bed, such as after seeds have been loaded and the cover 400 has been removed from the base 450.

Alignment features provide more secure interface between cover and base. For example, FIGS. 4A and 4B illustrate alignment features including engagement surface 454 that engages with surface 404, and outer surfaces 411 of cover 400 that engage with inner surfaces 461 of the base 450.

Although certain embodiments have been described with reference to the above examples, it will be understood that modifications and variations are encompassed within the spirit and scope of the invention.

OTHER EMBODIMENTS

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

It should be emphasized that many variations and modifications may be made to the above-described embodiments, the elements of which are to be understood as being among other acceptable examples. All such modifications and variations are intended to be included herein within the scope of this disclosure. The foregoing description details certain embodiments of the invention. It will be appreciated, however, that no matter how detailed the foregoing appears in text, the invention can be practiced in many ways. As is also stated above, the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A loading apparatus comprising:
a biocompatible radioactive seed carrier;
a base comprising:
a loading bed configured to support the radioactive seed carrier configured to receive one or more radioactive seed;
a base loading channel configured to receive an injection device, the injection device configured to inject the one or more radioactive seed into the radioactive seed carrier; and
a lid configured to engage with the base to create a loading chamber, the lid comprising:
a push block configured to exert force towards the loading bed of the base, wherein when a radioactive seed carrier is positioned on the loading bed the push block secures the radioactive seed carrier.

2. The loading apparatus of claim 1, wherein the radioactive seed carrier comprises collagen.

3. The loading apparatus of claim 1, wherein the push block is spring-loaded.

4. The loading apparatus of claim 1, wherein the radioactive seed carrier is configured for implantation into mammalian tissue.

5. A loading apparatus comprising:
a loading bed configured to support a biocompatible radioactive seed carrier configured to receive one or more radioactive seed;
a base loading channel configured to receive an injection device, the injection device configured to inject the one or more radioactive seed into the radioactive seed carrier; and
a lid configured to engage with the base to create a loading chamber, the lid comprising:
a push block configured to exert force towards the loading bed of the base, wherein when a radioactive seed carrier is positioned on the loading bed the push block secures the radioactive seed carrier; and
a lid loading channel substantially co-axial with the base loading channel when the lid is engaged with the base.

6. A loading apparatus comprising:
a loading bed configured to support a biocompatible seed carrier configured to receive a radioactive seed;
a loading channel configured to receive an injection device, the injection device configured to inject the radioactive seed into the biocompatible seed carrier;
one or more seed alignment windows positioned to provide visibility of at least a portion of the loading bed where the radioactive seed is positioned in the biocompatible seed carrier; and
a push block configured to exert force towards the loading bed, wherein when the biocompatible seed carrier is positioned on the loading bed the push block secures the biocompatible seed carrier.

7. A loading apparatus comprising:
a loading bed configured to support a biocompatible seed carrier configured to receive a radioactive seed;
a loading channel configured to receive an injection device, the injection device configured to inject the radioactive seed into the biocompatible seed carrier;
one or more carrier alignment windows positioned to provide visibility of at least a portion of the loading bed where the biocompatible seed carrier is positioned; and
a push block configured to exert force towards the loading bed, wherein when the biocompatible seed carrier is positioned on the loading bed the push block secures the biocompatible seed carrier.

8. A method of loading a radioactive seed into a biocompatible carrier, the method comprising:
positioning a biocompatible carrier onto a loading bed of a loading base, wherein the biocompatible carrier is configured to receive a radioactive seed;
positioning a lid onto the loading base so that a push block of the lid is positioned to exert force onto the biocompatible carrier positioned on the loading bed of the loading base; and
inserting an injection device into a loading channel of the loading base, wherein the injection device is configured to move at least partially through the loading channel and deposit the radioactive seed into the biocompatible carrier.

9. The method of claim 8, wherein the push block is spring-loaded.

10. The method of claim 8, wherein the biocompatible carrier consists essentially of collagen.

11. The method of claim 8, wherein the biocompatible carrier is configured for implantation into mammalian tissue.

12. A loading apparatus comprising:
- a loading bed configured to support a first surface of a biocompatible seed carrier, the biocompatible seed carrier having a second surface opposing the first surface and defining a thickness therebetween;
- a loading channel configured to receive an injection device, the injection device configured to inject a radioactive seed into the thickness of the biocompatible seed carrier; and
- a push block configured to exert force towards the loading bed, wherein when the biocompatible seed carrier is positioned on the loading bed the push block exerts force onto the second surface of the biocompatible seed carrier to secure the biocompatible seed carrier.

13. The loading apparatus of claim 12, wherein the push block is spring-loaded.

14. The loading apparatus of claim 12, wherein the biocompatible seed carrier consists essentially of collagen.

15. The loading apparatus of claim 12, wherein the biocompatible seed carrier is configured for implantation into mammalian tissue.

\* \* \* \* \*